United States Patent [19]

Crews et al.

[11] Patent Number: 5,201,280
[45] Date of Patent: Apr. 13, 1993

[54] METHOD FOR PREFERENTIAL PRODUCTION OF FEMALE TURTLES, LIZARDS, AND CROCOIDLES

[75] Inventors: David Crews; Thane Wibbels, both of Austin, Tex.

[73] Assignee: Reproductive Sciences, Inc., Austin, Tex.

[21] Appl. No.: 500,777

[22] Filed: Mar. 28, 1990

Related U.S. Application Data

[63] Continuation-in-part of Ser. No. 361,930, Jun. 6, 1989, abandoned.

[51] Int. Cl.$^5$ .................. A01K 67/00; C12N 15/00; A61K 31/565
[52] U.S. Cl. ........................... 119/174; 800/2; 800/DIG. 6; 119/30; 514/182; 435/240.2
[58] Field of Search ............... 119/1, 30, 174; 800/2, 800/DIG. 6; 435/240.2, DIG. 6, 172.1; 514/182, 26

[56] References Cited

U.S. PATENT DOCUMENTS

| | | | |
|---|---|---|---|
| 4,334,500 | 6/1982 | Ziller | 119/15 |
| 4,469,047 | 9/1984 | Miller | 119/1 |
| 4,593,646 | 6/1986 | Miller | 119/1 |
| 4,701,450 | 10/1987 | Kelder et al. | 514/177 |

OTHER PUBLICATIONS

Crews et al., 1989, Gen. Comp. Endocrinol. 76, 159–166.
Bull, J. J. 1980. Qtrly. Rev. Biol. 53, 3–21.
Bogart M. H. 1987. J. Theoret. Biol. 128, 349–347.
Gutzke, et al. 1988 Gen. Comp. Endocrinol. 71, 265–267.
Gutzke et al. 1986 Gen. Comp. Endocrinol. 64, 368–372.
Bull et al. 1988 Gen. Comp. Endocrinol. 70, 425–428.

*Primary Examiner*—Christopher S. F. Low
*Attorney, Agent, or Firm*—Ansel M. Schwartz

[57] ABSTRACT

A method for sex reversal in reptiles and their derivatives comprising the steps of sterilizing the surface of a fertilized egg; injecting the egg with a material that causes sex reversal at least before the first two-thirds of incubation of the egg has passed; and sealing any holes in the egg. In a preferred embodiment, the material that causes sex reversal includes natural estrogens or its synthetic mimics. In an alternative embodiment, the material is applied to the surface of the egg. By practicing the aforesaid method, sex reversal in reptiles and their derivatives is accomplished and viable all female sexed hatchlings are capable of being produced thereby.

4 Claims, No Drawings

METHOD FOR PREFERENTIAL PRODUCTION OF FEMALE TURTLES, LIZARDS, AND CROCOIDLES

CROSS REFERENCE

This is a continuation-in-part application of U.S. patent Ser. No. 07/361,930 filed Jun. 6, 1989, now abandoned.

FIELD OF THE INVENTION

The present invention relates to the sex reversal of reptiles and their derivatives. More specifically, the present invention relates to the sex reversal of reptiles and their derivatives by injection of a sex reversing material at least before the first two-thirds of incubation has passed.

BACKGROUND OF THE INVENTION

Many turtles and lizards, and all crocodilians, are known to have temperature-dependent sex determination (TSD)(Bull, 1980). Instead of an individual's sex being determined by specific sex chromosomes, sex is determined in species with TSD by the temperature at which the egg is incubated. Because of TSD, it becomes important to determine the impact of present management practices on the conservation of endangered turtle species. Evidence to date indicates that previous efforts may have produced mainly males, thereby hindering conservation and recovery efforts. In addition, the incubation of turtle eggs at temperatures that will consistently produce females usually results in significant thermally-induced mortality. The method of the present invention represents an alternative for producing female individuals without thermal mortality. Further, these estrogen-treated individuals are fertile as adults. When applied to endangered reptiles species, this technique would significantly improve the recovery of wild populations by skewing the population sex ratio to one that favors reproductive females.

SUMMARY OF THE INVENTION

The present invention pertains to a method for sex reversal in reptiles and their derivatives. The method comprises the steps of sterilizing the surface of a fertilized egg; injecting the egg with a material that causes sex reversal at least before the first two-thirds of incubation of the egg has passed; and sealing any holes in the egg. In a preferred embodiment, the material that causes sex reversal includes natural estrogens or its synthetic mimics. In an alternative embodiment, the material is applied to the surface of the egg.

By practicing the aforesaid method, sex reversal in reptiles and their derivatives is accomplished and viable, all female sexed hatchlings are capable of being produced thereby.

DESCRIPTION OF THE PREFERRED EMBODIMENT

The present invention pertains to a method for sex reversal in reptiles and their derivatives. Reptiles and their derivatives include archosaurs (crocodilians and birds), anapsida (turtles) and lepidosauria (snakes and lizards). The method comprises the steps of: sterilizing the surface of a fertilized egg; injecting the egg with a material that causes sex reversal at least before the first two-thirds of incubation of the egg has passed; and sealing any holes in the egg. Note that each species has a known incubation period.

The material that causes sex reversal in reptiles and their derivatives includes natural estrogens or its synthetic mimics. Preferably, the material is estradiol-17 beta. A solution may, for example, be comprised of three to one hundred micrograms of estradiol-17 beta preferably dissolved in ten microliters of 95% alcohol. This solution is then injected into the egg at least before the first two-thirds of incubation of the egg has passed. The material is injected into the egg with, for instance, a syringe. The hole that is caused in the shell of the egg by the use of the syringe is preferably sealed by melting wax over any holes in the egg.

The second step of sterilizing the egg surface includes the step of painting at least a portion of the egg with an antibacterial and antifungal agent. Preferably, the step of injecting occurs at the portion of the egg that has been painted with an antibacterial and antifungal agent.

A step of sterilizing the surface of a fertilized egg should occur at least before the first two-thirds of incubation has passed. Similarly, the step of injecting the egg with the material that causes sex reversal preferably occurs immediately after the step of sterilizing the surface of the egg. Then, preferably immediately after the injecting step, the step of sealing any holes in the egg preferably occurs. At that point, the egg is then incubated until hatching occurs. The time frame for these steps should be short enough that there is little or no chance of the fertilized egg sustaining damage in any way. Thus, if sex-reversed males are mated with normal males, viable offspring result.

EXAMPLE

Eggs from the painted turtle (*Chrysemys picta*) were injected at Stage 17-19 of embryonic development (at least before the first two-thirds of incubation has passed). Injections consisted of a 5 microliter bolus of estradiol-17 beta at a concentration of 10 micrograms/microliter dissolved in 95% ethanol; the injection dosage therefore was 50 micrograms of estradiol-17 beta. Injections were performed using a 30 gauge needle attached to a Hamilton microliter syringe. Eggs were incubated at 25±1° C., a temperature that produces only male offspring in this species. Twelve eggs received estradiol-17 beta and 23 eggs received an injection of the vehicle (95% ethanol) only. All offspring from eggs injected with estradiol-17 beta were female and all offspring from eggs receiving the control injection were male.

In an alternative embodiment, a 5 microliter bolus consisting of 95% ethanol and hormone is applied directly to eggshell at least before the first two-thirds of incubation. Sterilization of eggshell surface is not necessary. The amount of hormone is one to one hundred micrograms of natural estrogens or its synthetic mimics.

EXAMPLE

Eggs from the slider turtle (*Trachyemys scripta*) were treated at Stage 15-17 of embryonic development (at least before the first two-thirds of incubation had passed). Hormone administration consisted of topical application of a 5 microliter bolus of estradiol-17 beta at a concentration of 0.1, 1.0, 10.0 or 20.0 micrograms dissolved in 5 microliters of 95% ethanol. Administration was accomplished by spotting the hormone on the eggshell using a Hamilton microliter syringe. Eggs were incubated at 26 (±1) degree centigrade, a temperature that produces only male offspring in this species. The following numbers of individuals were treated with hormone: 0.1 micrograms=15, 1.0 micrograms=15, 10.0 micrograms=15, 20.0 micrograms=12. Nine individuals were treated with the vehicle (95% ethanol) only. Seven of the individuals receiving 0.1 micrograms and six of the individuals receiving 1.0 micrograms were female whereas all of the individuals receiving 10.0 or 20.0 micrograms were female; all offspring from eggs receiving the control vehicle were male.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for preferential production of female turtles, lizards or crocodiles which have temperature dependent sex determination by treating the developing embryos in ovo, comprising the steps of:
   (1) spotting an effective amount of an estrogen into the surface of the turtle, lizard, or crocodile eggshell so as to effect development of female gonads in the developing embryo; and,
   (2) incubating the eggs at a temperature known to effect development of male gonads until hatch and thereby obtain viable female turtles, lizards, or crocodiles.

2. The method of claim 1 wherein the spotting step (1) occurs before the first two-thirds of the incubation has passed.

3. The method of claim 2 which includes before the spotting step, the preparation of a bolus of an estrogen in 95% ethanol, which bolus is applied to the surface of the eggshell.

4. The method of claim 3, wherein the bolus of estrogen is 5 microliters and of the hormone is 1 to 100 micrograms of an estrogen.

* * * * *